(12) United States Patent
Le

(10) Patent No.: US 11,793,879 B2
(45) Date of Patent: Oct. 24, 2023

(54) MONOLITHIC COMPOSITION FOR DUAL-RATE RELEASE WITH HIGH DRUG LOADING

(71) Applicant: Matripharm International Inc., Laval (CA)

(72) Inventor: Tien Canh Le, Montréal (CA)

(73) Assignee: MATRIPHARM INTERNATIONAL INC., Laval (CA)

( * ) Notice: Subject to any disclaimer, the term of this patent is extended or adjusted under 35 U.S.C. 154(b) by 108 days.

(21) Appl. No.: 17/405,610

(22) Filed: Aug. 18, 2021

(65) Prior Publication Data

US 2021/0379187 A1 Dec. 9, 2021

Related U.S. Application Data

(63) Continuation of application No. 16/079,004, filed as application No. PCT/CA2017/050225 on Feb. 23, 2017, now abandoned.

(60) Provisional application No. 62/298,755, filed on Feb. 23, 2016.

(51) Int. Cl.

| | |
|---|---|
| C08B 11/12 | (2006.01) |
| C08B 31/12 | (2006.01) |
| C08B 37/00 | (2006.01) |
| A61K 47/36 | (2006.01) |
| A61K 9/20 | (2006.01) |
| A61K 31/167 | (2006.01) |
| A61K 31/522 | (2006.01) |
| A61K 47/38 | (2006.01) |

(52) U.S. Cl.
CPC ............. *A61K 47/36* (2013.01); *A61K 9/205* (2013.01); *A61K 9/2027* (2013.01); *A61K 9/2054* (2013.01); *A61K 31/167* (2013.01); *A61K 31/522* (2013.01); *A61K 47/38* (2013.01); *C08B 11/12* (2013.01); *C08B 31/12* (2013.01); *C08B 37/0033* (2013.01); *C08B 37/0045* (2013.01); *C08B 37/0084* (2013.01)

(58) Field of Classification Search
None
See application file for complete search history.

(56) References Cited

U.S. PATENT DOCUMENTS

| | | | |
|---|---|---|---|
| 4,097,606 | A | 6/1978 | Chavkin et al. |
| 4,167,621 | A | 9/1979 | Tessier |
| 2003/0096003 | A1 | 5/2003 | Huang et al. |

FOREIGN PATENT DOCUMENTS

| | | |
|---|---|---|
| WO | 200047628 A2 | 8/2000 |
| WO | 2004048418 | 6/2004 |
| WO | 2012116434 A1 | 9/2012 |
| WO | 2013166575 A1 | 11/2013 |

OTHER PUBLICATIONS

He, CN 102775506 A, machine translation. (Year: 2012).*
International Search Report of PCT/CA2017/050225; dated Jun. 27, 2017; Mackenzie, A.
Supplementary European Search Report of EP17755676.8; dated Sep. 12, 2019; Friedrich, C.

* cited by examiner

*Primary Examiner* — Layla D Berry
(74) *Attorney, Agent, or Firm* — BENOIT & COTE INC.

(57) ABSTRACT

The present document describes a process for the preparation of a low functionalization polysaccharide having carboxyl groups, comprising a) swelling of a polysaccharide granule in boiling water or a water/polyol mixture, to obtain a swollen polysaccharide; b) partial gelatinization of said swollen polysaccharide in an alkaline solvent mixture of water and alcohol and/or polyol, to obtain a partially gelatinized polysaccharide; and c) partial functionalization of said partially gelatinized polysaccharide with a functionalizing agent, to obtain the low functionalization polysaccharide.

13 Claims, 3 Drawing Sheets

MONOLITHIC COMPOSITION FOR DUAL-RATE RELEASE WITH HIGH DRUG LOADING

CROSS-REFERENCE TO RELATED APPLICATIONS

This application is a continuation of U.S. patent application Ser. No. 16/079,004, filed on Aug. 22, 2018, which is a United States National Phase application under 35 USC § 371 of PCT/CA2017/050225, filed Feb. 23, 2017, which claims priority from and the benefit of U.S. provisional patent application No. 62/298,755, filed Feb. 23, 2016, the specifications of which are hereby incorporated by reference in their entireties.

BACKGROUND

(A) Field

The subject matter disclosed generally relates to a process to functionalize polysaccharides, preferably starch, using binary or ternary solvent mixtures. The obtained functionalized polysaccharide can be used as an excipient, under monolithic tablet dosage form, for controlled release, preferably for dual-rate release (DRR), with high loading of active pharmaceutical ingredient (API).

(b) Related Prior Art

Polysaccharides such as starch, cellulose, pectin, and others can be functionalized and used as excipient for dual rate release (DRR). However, starch is preferably used due to its low cost, biocompatibility and its non-toxicity. The functionalization of starch or other polysaccharides is preferably carboxylation, but it is also possible to functionalize them with hydroxypropylation, succinylation, ethylation, etc.

Generally, the process in the prior art is performed in an aqueous medium by etherification of the polysaccharide with sodium monochloroacetate, under alkaline conditions. In other processes, the functionalization was carried out in solvents such as methanol or ethanol in order to increase the degree of substitution (DS) of the polysaccharide. However, the obtained powder granules are fine and when compressed into tablets, they often break due to a lack of the cohesion. Furthermore, these excipients are used as disintegrating agents and they cannot be used for DRR with high active pharmaceutical ingredient (API) loading.

Therefore, there is a need for additional excipients to mitigate the disadvantages of the excipients of the prior art.

SUMMARY

According to an embodiment, there is provided a process for the preparation of a low functionalization polysaccharide having carboxyl groups, comprising:
a) swelling of a polysaccharide granule in boiling water or a water/polyol mixture, to obtain a swollen polysaccharide;
b) partial gelatinization of the swollen polysaccharide in an alkaline solvent mixture of water and alcohol and/or polyol, to obtain a partially gelatinized polysaccharide;
c) low functionalization of the partially gelatinized polysaccharide with a functionalizing agent under alkaline conditions, to obtain the functionalized polysaccharide, wherein the functionalized polysaccharide may have a degree of substitution of from about 0.1 to about 0.3.

The functionalized polysaccharide may have a degree of substitution of from about 0.2.

The polysaccharide may be chosen from a starch, a cellulose, a chitosan, a guar gum, a gellan gum, a xanthan gum, an agar, an agarose, an arabic gum, a pullulan, a dextran, a dextrin, a maltodextrin, a cyclodextrin and/or chosen from modified polysaccharides such as hydroxypropyl starch, hydroxypropyl cellulose, hydroxypropyl methyl starch, hydroxypropyl methyl cellulose, ethyl-cellulose, methyl-cellulose, succinyl starch, octenyl starch and combinations thereof.

The polyol may be from ethylene glycol, propylene glycol, glycerol, sorbitol or combinations thereof.

The alkaline solvent mixture of water and alcohol may be a binary solvent mixture of water and alcohol or ternary solvent mixture of water, alcohol and polyol.

The binary solvent mixture of water and alcohol comprises water and at least one of ethanol, methanol, isopropanol, or combinations thereof.

The ternary solvent mixture of water and alcohol comprises water, ethanol or methanol and propylene glycol or glycerol or propanol or combination thereof.

The water may be from about 5% to about 50% v/v of the binary or ternary solvent mixture.

The alcohol may be from about 5% to about 50% v/v of the ternary solvent mixture.

The polyol may be from about 50% to about 95% v/v of the binary or ternary solvent mixture.

The functionalizing agent may be sodium chloroacetate, succinic anhydride, n-Octenyl succinic anhydride, acrylic acid, and combinations thereof.

The functionalizing agent may be sodium chloroacetate.

The process may further comprise step c') after step c):
c') complexation of the functionalized polysaccharide with a divalent cation chosen from calcium, magnesium, zinc, aluminum, copper, or combinations thereof.

The process may further comprise step d):
d) filtration of the functionalized polysaccharide and resuspension in alcohol, to obtain a resuspended functionalized polysaccharide.

The process may further comprise step e):
e) neutralization of the resuspended functionalized polysaccharide, to obtain a neutralized functionalized polysaccharide.

The process may further comprise step f):
f) washing of the neutralized functionalized polysaccharide, to obtain a precipitated functionalized polysaccharide.

The process may further comprise step g):
g) drying of the precipitated functionalized polysaccharide, to obtain a dried functionalized polysaccharide.

The functionalization may be carboxymethylation.

According to another embodiment, there is provided a low functionalization polysaccharide prepared by the process of the present invention, having a degree of substitution of from about 0.1 to about 0.3.

The low functionalization polysaccharide may have a degree of substitution of about 0.2.

The low functionalization polysaccharide may be a carboxymethyl cellulose.

The low functionalization polysaccharide may be a xanthan, an alginate, a pectin, or combinations thereof.

According to another embodiment, there is provided a monolithic solid dosage form for dual rate release of an active pharmaceutical ingredient, comprising a low functionalization polysaccharide prepared by the process of the present invention, an anionic polysaccharide complexed with a divalent cation, a disintegrating agent and the active pharmaceutical ingredient.

The disintegrating agent may be cross-linked povidone, cross-linked carmellose, starch glycolate, or combinations thereof.

The monolithic solid dosage form may further comprise a sustained release agent.

The sustained release agent may be an amino acid combination.

The amino acid combination may be a combination of arginine and/or lysine.

The anionic polysaccharide complexed with a divalent cation may have a degree of substitution of from about 0.5 to about 1.5

The divalent cation may be chosen from calcium, magnesium, zinc, aluminum, copper, or combinations thereof.

The divalent cation may be calcium.

The following terms are defined below.

The term "amino acid" is intended to mean the organic compounds which contain amine (—NH2) and carboxylic acid (—COOH) functional groups, usually along with a side-chain specific to each amino acid. This include the 21 proteogenic alpha amino acids, alanine, valine, isoleucine, leucine, methionine, phenylalanine, tyrosine, tryptophan, serine, threonine, asparagine, glutamine, cysteine, selenocysteine, glycine, proline, arginine, histidine, lysine, aspartic acid, glutamic acid. This also includes beta, gamma, or delta amino acids suitable for the present invention.

As used herein, the term «functionalizing starch» or «functionalized starch» is intended to mean functionalization that is not limited to the conversion of the native or modified starch by carboxylation, but also includes possible functionalization of other starch derivatives such as carboxylation of starch succinate (succinyl starch), carboxylation of hydroxypropyl starch, carboxylation of acetyl starch, carboxylation of hydroxypropyl methyl starch, carboxylation of acid modified starch, carboxylation of octenyl starch, carboxylation of pregelatinized starch or mixture thereof.

The term «functionalization» as used herein is intended to mean the addition by covalent bonds of carboxyl groups (or its derivatives) onto the starch chains. The functionalization can be (but is not limited to) the carboxylation (addition of carboxylate groups), at the same time of the carboxylation, the amination (addition of amine groups), alkylation (addition of alkyl groups) or acylation (addition of acyl groups). In some embodiments, the functionalization may be low functionalization, referring to degrees of substitutions of between about 0.1 to about 0.3. In other embodiments, the functionalization may be higher, for example referring to degrees of substitutions of between about 0.5 to about 1.5.

The term «carboxylation» as used herein is intended to mean the addition of carboxyl groups onto the polysaccharide macromolecule. Possible carboxylation includes but not limited to the carboxymethylation, carboxyethylation, succinylation, octenyl succinylation, acrylation, etc. According to a preferred embodiment, the carboxylation is a «carboxymethylation».

The term «degree of substitution» is intended to mean the average number of substituents per glucose unit (GU), the monomer unit of starch/polysaccharide. Since each GU contains three hydroxyl groups, a low degree of substitution may refer to DS varying between about 0.10-0.3, or about 0.1-0.2, or about 0.2-0.3. According to an embodiment of the present invention, the DS may be equal to or greater than 0.10. In other embodiments, the degrees of substitutions may be higher (e.g. a high degree of substitution) and be between about 0.5 to about 1.5

The term "complexation" is intended to mean the process by which two or more ingredients are made with an anionic (i.e. carboxylate) polymer to form a complex.

The term «composition» as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
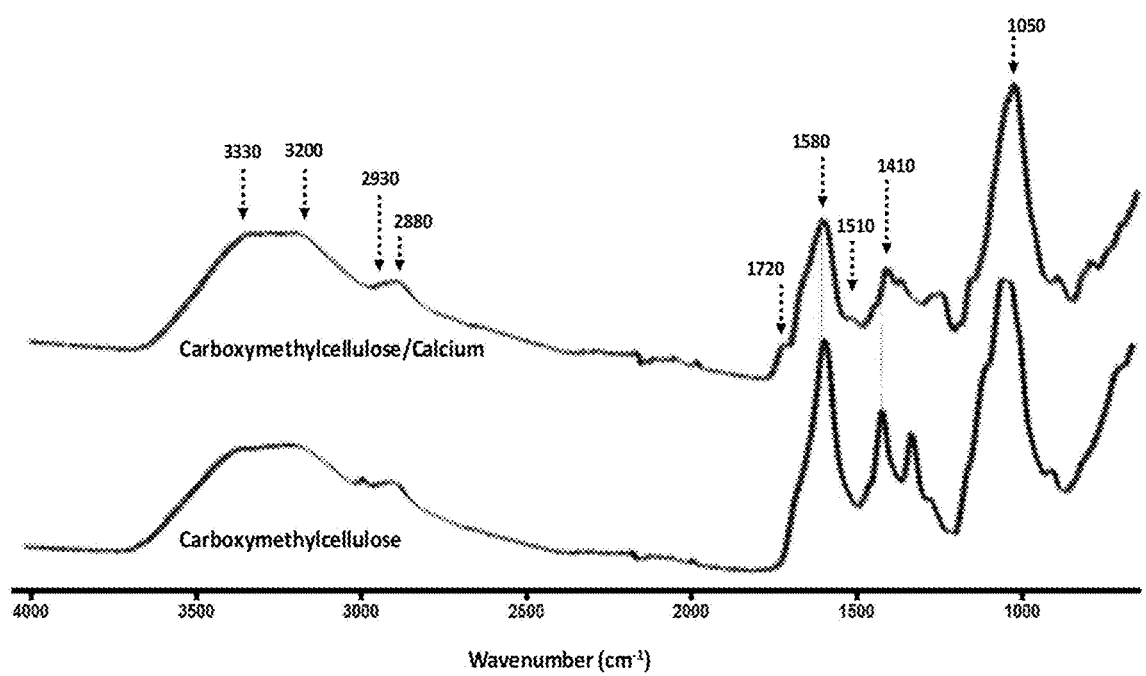
FIG. 1 illustrates a FTIR spectra of carboxymethyl cellulose and carboxymethyl cellulose/calcium complexes according to an embodiment of the present invention.

The present application describes a new process of functionalization, in particular carboxylation, of polysaccharides, preferably starch, by using binary or ternary solvent mixtures which provide powder granules possessing more cohesion and high stability under tablet form. In addition, when formulated with a disintegrating agent, the functionalized polysaccharide of the present invention can release the API in two different rates: immediate release and slow release.

In embodiments there is disclosed a process to functionalize polysaccharides with carboxyl groups such as carboxylation, succinylation, acrylation, and the likes, preferably starch using binary or ternary solvent mixtures. The obtained functionalized polysaccharide can be used as excipient, under monolithic tablet dosage form, for controlled release, preferably for dual-rate release (DRR), with high loading of active pharmaceutical ingredient (API) which can reach, for example up to 1000 mg.

According to an embodiment, the process for functionalization of polysaccharides of the present invention generally comprised three steps:
1) Swell the polysaccharide granules by incubation of starch during 30 minutes in a bath containing boiling water, and/or mixtures of water with for example ethylene glycol, propylene glycol and/or glycerol. This step is important to promote the granule surface contact with functionalizing agent and to favor the penetration of functionalizing agent inside the granules;
2) Partially gelatinize the polysaccharide in a binary (e.g. water/ethanol, water/methanol; water/isopropanol, and the likes) or a ternary (i.e. water/methanol/propylene glycol, water/methanol/ethanol; water/methanol/isopropanol; water/ethanol/isopropanol; water/ethanol/ethylene glycol; water/ethanol/propylene glycol; water/ethanol/glycerol, etc.) solvent mixtures under alkaline condition; In these mixtures, water may be present at about 5% to 50% v/v, or from about 10% to 50%, or from about 15% to about 50%, or from about 20% to about 50%, or from about 25% to about 50%, or from about 30% to about 50%, or from about 35% to about 50%, or from about 40% to about 50%, or from about 45% to about 50%, or about 5% to about 45% v/v, or from about 10% to about 45%, or from about 15% to about 45%, or from about 20% to about 45%, or from about 25% to about 45%, or from about 30% to about 45%, or from about 35% to about 45%, or from about 40% to about 45%, or about 5% to about 40% v/v, or from about 10% to about 40%, or from about 15% to about 40%, or from about 20% to about 40%, or from about 25% to about 40%, or from about 30% to about 40%, or from about 35% to about 40%, or 5% to 35% v/v, or from about 10% to about 35%, or from about 15% to about 35%, or from about 20% to about 35%, or from about 25% to about 35%, or from about 30% to about 35%, or 5% to 30% v/v, or from about 10% to about 30%, or from about 15% to about 30%, or from about 20% to about 30%, or from about 25% to about 30%, or 5% to 25% v/v, or from about 10% to about 25%, or from about 15% to about 25%, or from about 20% to about 25%, or from about 5% to about 20% v/v, or from about 10% to about 20%, or from about 15% to about 20%, or about 5% to about 15% v/v, or from about 10% to about 15%, or about 5% to about 10% v/v of the mixture, and the alcohols may be present from about 50% to about 95%, or about 55% to about 95%, or about 60% to about 95%, or about 65% to about 95%, or about 70% to about 95%, or about 75% to about 95%, or about 80% to about 95%, or about 85% to about 95%, or about 90% to about 95%, or about 50% to about 90%, or about 55% to about 90%, or about 60% to about 90%, or about 65% to about 90%, or about 70% to about 90%, or about 75% to about 90%, or about 80% to about 90%, or about 85% to about 90%, or about 50% to about 85%, or about 55% to about 85%, or about 60% to about 85%, or about 65% to about 85%, or about 70% to about 85%, or about 75% to about 85%, or about 80% to about 85%, or about 50% to about 80%, or about 55% to about 80%, or about 60% to about 80%, or about 65% to about 80%, or about 70% to about 80%, or about 75% to about 80%, or about 50% to about 75%, or about 55% to about 75%, or about 60% to about 75%, or about 65% to about 75%, or about 70% to about 75%, or about 50% to about 70%, or about 55% to about 70%, or about 60% to about 70%, or about 65% to about 70%, or about 50% to about 65%, or about 55% to about 65%, or about 60% to about 65%, or about 50% to about 60%, or about 55% to about 60%, or about 50% to about 55% v/v the mixture. Polyols (ethylene glycol, propylene glycol and/or glycerol) may be present at about 5 to 50% v/v, or from about 10% to about 50%, or from about 15% to about 50%, or from about 20% to about 50%, or from about 25% to about 50%, or from about 30% to about 50%, or from about 35% to about 50%, or from about 40% to about 50%, or from about 45% to about 50%, or about 5% to about 45% v/v, or from about 10% to about 45%, or from about 15% to about 45%, or from about 20% to about 45%, or from about 25% to about 45%, or from about 30% to about 45%, or from about 35% to about 45%, or from about 40% to about 45%, or about 5% to about 40% v/v, or from about 10% to about 40%, or from about 15% to about 40%, or from about 20% to about 40%, or from about 25% to about 40%, or from about 30% to about 40%, or from about 35% to about 40%, or 5% to 35% v/v, or from about 10% to about 35%, or from about 15% to about 35%, or from about 20% to about 35%, or from about 25% to about 35%, or from about 30% to about 35%, or 5% to 30% v/v, or from about 10% to about 30%, or from about 15% to about 30%, or from about 20% to about 30%, or from about 25% to about 30%, or 5% to 25% v/v, or from about 10% to about 25%, or from about 15% to about 25%, or from about 20% to about 25%, or about 5% to about 20% v/v, or from about 10% to about 20%, or from about 15% to about 20%, or about 5% to about 15% v/v, or from about 10% to about 15%, or about 5% to about 10% v/v of the mixture. The binary solvent system contains water and alcohol. As alcohol (e.g. methanol) may dehydrate and are often used in large amount (e.g. 80% v/v), they can dehydrate the granules of the starch during the reaction. The addition of propylene glycol or glycerol or ethylene glycol allows reducing the dehydration property, such as glycols agents can stabilize with starch or alcohol thereby preventing the phenomenon of dehydration.

3) Functionalize the polysaccharide by adding functionalizing agent and the reaction is carried out at ambient temperature (23±0.5° C.) for at least 18 h. The functionalization is partial, yielding a polysaccharide that has a low degree of substitution (i.e. a low functionalization polysaccharide), from about 0.1 to 0.3, or about 0.15 to 0.3, or 0.2 to 0.3. or about 0.25 to 0.3, or about 0.1 to 0.25, or about 0.15 to 0.25, or about 0.2 to 0.25, or about 0.1 to 0.2, or about 0.15 to 0.2, or about 0.1 to 0.15, or about 0.1, 0.15, 0.2, 0.25, 0.3. Functionalizing agents include but are not limited to sodium chloroacetate, succinic anhydride (for succinyl polysaccharide), n-Octenyl succinic anhydride (for octenyl succinyl polysaccharide), acrylic acid (for carboxyethyl polysaccharide).

At the end of the reaction, the functionalized polysaccharide is filtered and the precipitate is resuspended in alcohol, preferably ethanol 80% v/v and neutralized with an organic acid (e.g. acetic acid) at pH value of about 6.8. To obtain powders, the precipitate is washed twice in ethanol 80% v/v to remove all the by-products and non-reacted functionalizing agent and finally with ethanol 95% v/v before drying by incubation at 40° C. overnight in an oven.

According to an embodiment, the functionalization is carboxymethylation.

According to another embodiment, the polysaccharide is a starch, a cellulose, a chitosan, a guar gum, a gellan gum, a xanthan gum, an agar, an agarose, an arabic gum, a pullulan, a dextran, a dextrin, a maltodextrin, a cyclodextrin, and/or chosen from modified polysaccharides such as hydroxypropyl starch, hydroxypropyl cellulose, hydroxypropyl methyl starch, hydroxypropyl methyl cellulose, ethyl-cellulose, methyl-cellulose, succinyl starch, octenyl starch and combinations thereof.

According to another embodiment, the process for functionalization of polysaccharides of the present invention generally comprised following three steps when the functionalization is carboxymethylation and the polysaccharide is starch:

1) Swell starch granules by incubation of starch during 30 minutes in a bath containing boiling water and/or mixtures of water with for example ethylene glycol, propylene glycol and/or glycerol. This step is important to promote the granule surface contact with functionalizing agent and to favor the penetration of functionalizing agent inside the starch granules;

2) Partially gelatinize starch in binary (i.e. water/ethanol, water/methanol; water/isopropanol, and the likes) or a ternary (i.e. water/methanol/propylene glycol, water/methanol/ethanol; water/methanol/isopropanol; water/ethanol/isopropanol; water/ethanol/ethylene glycol; water/ethanol/propylene glycol; water/ethanol/glycerol, etc.) solvent mixtures under alkaline condition; In these mixtures, water may be present at about 5 to 50% v/v of the mixture, and the alcohols may be present from about 50 to 95% v/v of the mixture. Polyols (ethylene glycol, propylene glycol and/or glycerol) may be present at about 5 to 50% v/v of the mixture. The binary solvent system contains water and alcohol. As alcohol (i.e. methanol) may dehydrate and are often used in large amount (e.g. 80% v/v), they can dehydrate the granules of the starch during the reaction. The addition of propylene glycol or glycerol or ethylene glycol allows to reduce the dehydration property (such glycols agents can stabilize with starch or alcohol thereby preventing the phenomenon of dehydration;

3) Carboxylate the starch by adding a functionalizing agent (e.g. sodium chloroacetate) and the reaction is carried out at ambient (room, about 24° C.) temperature for at least 12 h.

At the end of the reaction, the carboxymethyl starch is filtered and the precipitate is resuspended in alcohol, preferably ethanol 80% v/v and neutralized with an organic acid (e.g. acetic acid) at pH value of about 6.8. To obtain powders, the precipitate is washed twice in ethanol 80% v/v to remove all the by-products and non-reacted sodium chloroacetate and finally with ethanol 95% v/v before being incubated at 40° C. overnight in an oven.

According to another embodiment, the present invention also includes functionalized polysaccharides prepared by the process of the present invention.

Complexation of Functionalized Polysaccharide with Divalent Cations

For certain applications, functionalized polysaccharides such as carboxymethyl starch can be complexed with bivalent cations, preferably calcium ion. These complexed anionic polysaccharides can be combined with the low functionalization polysaccharide obtained by the process of the present invention, for example in dosage forms. The process of complexation can operate in the same solvent, binary or ternary solvent mixtures used for the preparation of the low functionalization polysaccharide of the present invention. Indeed, functionalized polysaccharides such as carboxymethyl starch may be suspended in the binary or ternary solvent mixture containing an excess of calcium, previously dispersed therein. After homogenous stirring during 30 minutes, the functionalized polysaccharide and divalent cations (e.g. carboxymethyl starch/calcium) complex is recovered by decantation or filtration. To obtain the complex powders, the drying process is carried out in the same conditions as described previously for drying of the functionalized polysaccharide.

In embodiments, these anionic polysaccharides complexed with divalent cations may have degrees of substitution higher than the low functionalization polysaccharide produced by the process of the present invention. Indeed, they may have degrees of substitutions of from about 0.5 to about 1.5, or about 0.6 to about 1.5, or about 0.7 to about 1.5, or about 0.8 to about 1.5, or about 0.9 to about 1.5, or about 1.0 to about 1.5, or about 1.1 to about 1.5, or about 1.2 to about 1.5, or about 1.3 to about 1.5, or about 1.4 to about 1.5, or 0.5 to about 1.4, or about 0.6 to about 1.4, or about 0.7 to about 1.4, or about 0.8 to about 1.4, or about 0.9 to about 1.4, or about 1.0 to about 1.4, or about 1.1 to about 1.4, or about 1.2 to about 1.4, or about 1.3 to about 1.4, or 0.5 to about 1.3, or about 0.6 to about 1.3, or about 0.7 to about 1.3, or about 0.8 to about 1.3, or about 0.9 to about 1.3, or about 1.0 to about 1.3, or about 1.1 to about 1.3, or about 1.2 to about 1.3, or 0.5 to about 1.2, or about 0.6 to about 1.2, or about 0.7 to about 1.2, or about 0.8 to about 1.2, or about 0.9 to about 1.2, or about 1.0 to about 1.2, or about 1.1 to about 1.2, or 0.5 to about 1.1, or about 0.6 to about 1.1, or about 0.7 to about 1.1, or about 0.8 to about 1.1, or about 0.9 to about 1.1, or about 1.0 to about 1.1, 0.5 to about 1.0, or about 0.6 to about 1.0, or about 0.7 to about 1.0, or about 0.8 to about 1.0, or about 0.9 to about 1.0, or 0.5 to about 0.9, or about 0.6 to about 0.9, or about 0.7 to about 0.9, or about 0.8 to about 0.9, or 0.5 to about 0.8, or about 0.6 to about 0.8, or about 0.7 to about 0.8, or 0.5 to about 0.7, or about 0.6 to about 0.7, or 0.5 to about 0.6.

According to an embodiment, at least 30% of the carboxyl groups may be complexed with a divalent cation. According to an embodiment, at least 40%, or 50%, or 60%, or 70%, or 80%, or 90% of the carboxyl groups being complexed with a divalent cation. The divalent cation may be chosen from calcium, magnesium, zinc, aluminum, copper, or combinations thereof.

Monolithic Tablet Formulation for Dual Rate Release

According to an embodiment, there is disclosed a dual release rate formulation which may comprise:
 a) a low functionalization polysaccharide of the present invention;
 b) a disintegrating agent;
 c) an amino acid;
 d) an active pharmaceutical ingredient.

The formulation may contain:
 1) Low functionalization polysaccharide used as excipient to stabilize tablet, preferably carboxymethyl starch or carboxymethyl cellulose, or carboxymethyl cellulose/calcium complex, or carboxymethyl starch/calcium complex, or mixture thereof;
 2) An anionic polysaccharide complexed with a divalent cation;
 3) A disintegrating agent such as crospovidone, croscarmellose and/or starch glycolate, preferably crospovidone to favor the immediate release;
 4) In some embodiments, an amino acid or a combination of amino acid, preferably arginine and lysine, for sustained release;
 5) An API which could be reached up to at least 1000 mg.

The combination of the low functionalization polysaccharide synthesized in a solvent, according to the process of the present invention, combined with the anionic polysaccharide complexed with a divalent cation, and a disintegrating agent results in a DRR. The present invention will be more readily understood by referring to the following examples which are given to illustrate the invention rather than to limit its scope.

Example 1

Carboxymethylation of Starch Using Binary Solvent Mixture 1-1 Swelling of Starch An amount of 150 g of starch, preferably high amylose corn starch is introduced in 2 L of boiling water for 30 minutes under mild stirring. When the temperature is cooled down to room temperature, the stirring is stopped and the reaction mixture is left to stand for at least 1 h to favor the precipitation of starch. The water is removed by decantation or by filtration.

Alternatively, an amount of 150 g of starch, preferably high amylose corn starch is introduced in 2 L of boiling water/glycerol for 30 minutes under mild stirring. When the temperature is cooled down to room temperature, the stirring is stopped and the reaction mixture is left to stand for at least 1 h to favor the precipitation of starch. The water is removed by decantation or by filtration.

1-2 Gelatinization of Starch

After the swelling of starch as described above, starch is partially gelatinized by adding 1 L of binary (water/ethanol, 20:80 v/v) solvent mixture for 10 minutes at room temperature. Then, an amount of 110 g of NaOH is added in the solvent mixture under vigorous stirring for at least 15 minutes or until obtaining a homogenous suspension.

1-3 Functionalization of Starch

After gelatinization of starch, the carboxymethylation is performed by introducing an amount of 150 g of sodium chloroacetate directly in the suspension, always under vigorous stirring. The reaction is continued for at least 16 h at 40° C., and it may also be performed at the room temperature for 24 h.

At the end of the reaction, the precipitate is separated by filtration (or by decantation) and washed with 2 L of ethanol 80% v/v, under strong stirring to remove a maximum of the alkaline medium and by-products. After filtration, the precipitate is resuspended in ethanol 80% v/v and the neutralization is performed by using acetic acid until a pH value between 6.5 and 7.0 is reached. Finally, the precipitate is collected and washed with 2 L of ethanol (80% v/v) followed one more time in ethanol 95% v/v before drying at 40° C. overnight to obtain the carboxymethyl starch powders.

Example 2

Carboxymethylation of Starch Using Ternary Solvent Mixture

The carboxymethylation of starch using ternary solvent mixture can be conducted under similar conditions for binary solvent mixture, as described previously in Example 1, except that the ternary solvent mixture can be composed of water/ethanol/propylene glycol (10/80/10, v/v/v) or water/ethanol/isopropanol (20/40/40, v/v/v) have been used instead of binary solvent.

These carboxymethyl starches from example 1 and 2 possess a degree of substitution (DS) between 0.20-0.25

Example 3

Preparation of Carboxymethyl Cellulose/Calcium Complex

An amount of 20 g of carboxymethyl cellulose (CMC, MW 150 kDa, DS 0.7) is introduced in 120 mL of absolute ethanol. Thereafter, a volume of 80 ml of calcium solution 7.5% w/w is added in the suspension, under strong stirring. After 1 h, the carboxymethyl cellulose/calcium complex is separated by decantation or by filtration and the complex is washed in ethanol 80% for 30 minutes. Finally, the complex powder is collected and dried in ethanol 95% before incubation in the oven for at least 24 h at 40° C.

FTIR Analysis shows that CMC possesses absorption bands at 1580 and 1410 $cm^{-1}$ assigned to carboxylate anions (asymmetric and symmetric stretching vibrations). When CMC complexed with calcium, a moderate decrease of the intensities for absorption bands at 1587 and 1410 $cm^{-1}$ is observed due to complexion of carboxylate groups with calcium which cause a new absorption band appearance at 1720 $cm^{-1}$.

Example 4

DRR Kinetic Profile Used Carboxymethyl Starch as Excipient and Acetaminophen as Tracer 4-1 Formulation for Monolithic Tablet Dosage Form

| | |
|---|---|
| Acetaminophen | 1000 mg |
| Carboxymethyl starch | 150 mg |

-continued

| | |
|---|---|
| Carboxymethylcellulose/Ca | 40 mg |
| Crospovidone | 35 mg |
| Arginine | 35 mg |
| Lysine | 65 mg |
| Magnesium stearate | 15 mg |
| Total | 1340 mg |

In this case, the Acetaminophen/Excipient Ratio is about of 75:25. The Carboxymethyl starch is prepared according to the process of the present invention.

4-2 Preparation of Monolithic Tablet

Monolithic tablets using carboxymethyl starch synthesized as described above and containing 1000 mg (~75%) of acetaminophen as a tracer were obtained by direct compression of powders (2.3 T/cm$^2$) in a Carver hydraulic press.

4-3 Dissolution Assay

The dissolution kinetic assay is followed with a Distek™ apparatus according to the paddle method from USP-32, with slight modification. Indeed, the monolithic tablets are placed in 750 mL of simulated gastric fluid (SGF, pH 1.5) during 30 minutes, at 37° C. Thereafter, a volume of 250 mL of sodium tripolyphosphate 0.20 M is added directly in SGF to neutralize the gastric acidity for pH values of about 6.8-7.0 which constituted the pH of simulated intestinal fluid (SIF).

At different intervals of 30 minutes, an aliquot of 1 mL of dissolution fluid is withdrawn from dissolution media, filtered and properly diluted (approximately 1/50). The absorbency is measured with an UV spectrometer (Lambda-40 Spectrometer, Perkin Elmer) at 247 nm.

4-4 Results

Figure 2:
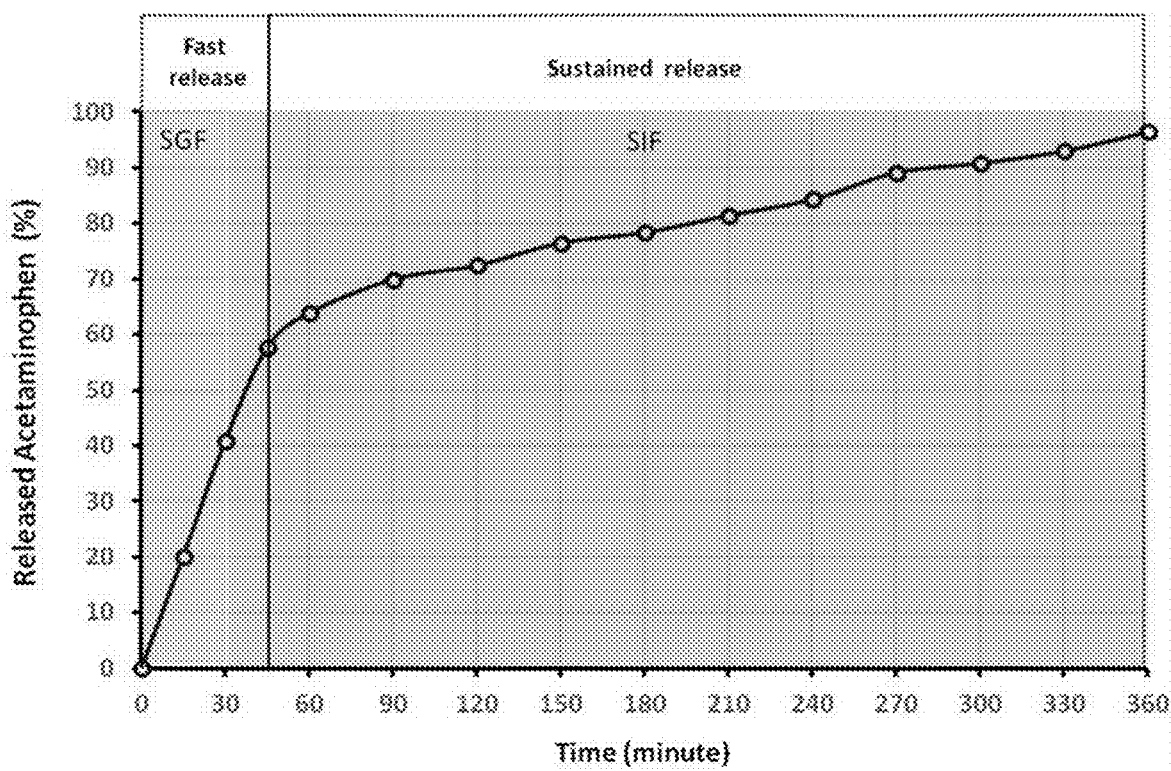
FIG. 2 illustrates the release kinetic profile of acetaminophen (1000 mg) from a tablet prepared with a carboxymethyl starch prepared by the process of the present invention.
Figure 3:
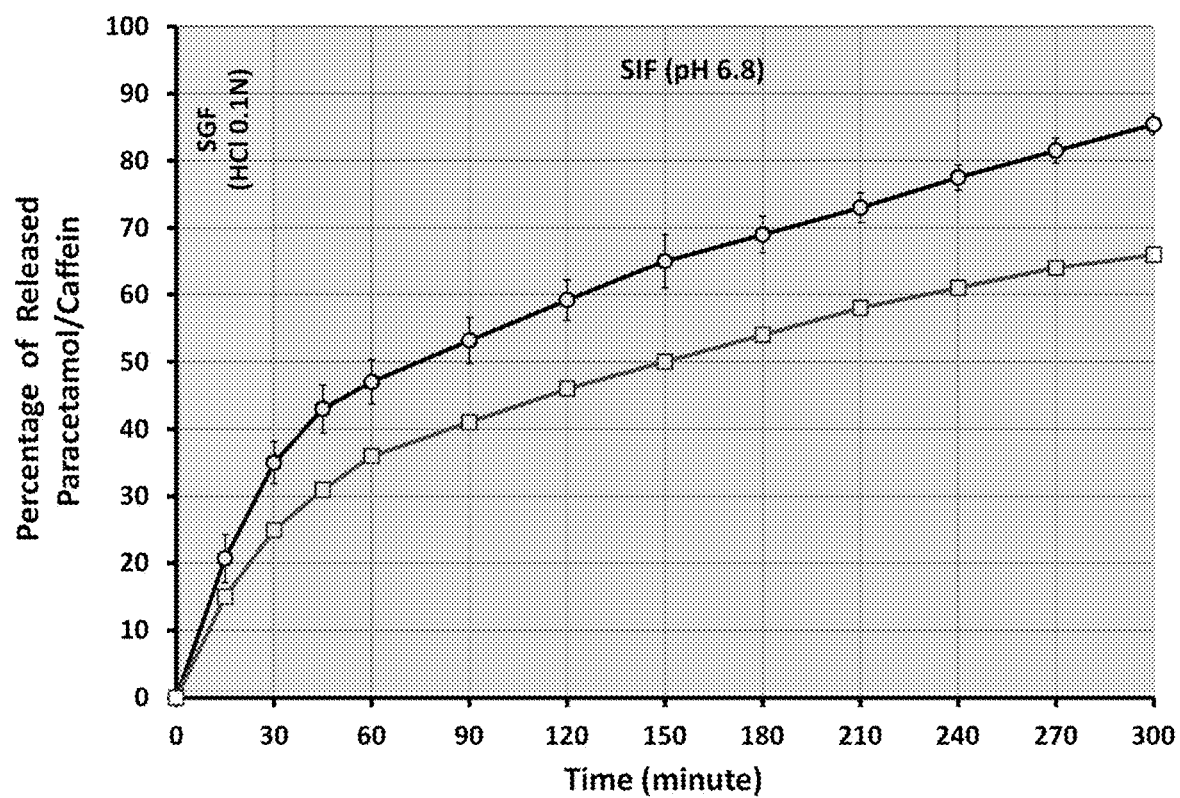
FIG. 3 illustrates the release kinetic profile of acetaminophen (900 mg) and caffeine (100 mg) from a tablet formulated with a carboxymethyl starch and Carboxymethyl cellulose/Calcium complex prepared by the process of the present invention.

Now referring to FIG. 2, data analysis shows that the immediate release of Acetaminophen is about of 60% (600 mg of Acetaminophen) after 45 minutes (30 minutes in SGF and 15 minutes in SIF). The remaining quantity of Acetaminophen is slowly released in SIF for a period approximately 5 h or more.

Example 5

DRR Kinetic Profile Used Carboxymethyl Starch as Excipient for Acetaminophen and Caffeine Combination 5-1 Formulation for Monolithic Tablet Dosage Form

| | |
|---|---|
| Acetaminophen | 900 mg |
| Caffeine | 100 mg |
| Carboxymethyl starch | 130 mg |
| Carboxymethylcellulose/Calcium | 30 mg |
| Hydroxypropylmethyl cellulose (E5) | 60 mg |
| Arginine | 20 mg |
| Magnesium stearate | 20 mg |
| Total | 1260 mg |

The Carboxymethyl starch is prepared according to the process of the present invention. The preparation of monolithic tablet and dissolution assay are conducted under similar conditions as described previously in the Example 4, section 4-1 and 4-2. For acetaminophen, the absorbency of samples is measured with an UV spectrometer at 247 nm. For caffeine, the dosage is carried out by HPLC according to method described by Hassouna et al. (Hassouna, M. E. M, Issa, Y. M. and Zayed, A. G. 2012. *J. Appl. Pharm. Sci.*, 02, 52-59)

5-2—Results

Data analysis shows that the immediate release of Acetaminophen is about of 35% (350 mg) of Acetaminophen and about of 25% (25 mg) of caffeine after 30 minutes in SGF. The remaining quantities of Acetaminophen and caffeine are slowly released in SIF for a period approximately 5 h or more.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A process for the preparation of a low functionalization polysaccharide having carboxyl groups, comprising:
    a) swelling of a polysaccharide granule in boiling water or a boiling water/polyol mixture, to obtain a swollen polysaccharide;
    b) partial gelatinization of said swollen polysaccharide in an alkaline solvent mixture of water and alcohol and/or polyol to obtain a suspension of a partially gelatinized polysaccharide;
    c) low functionalization of said partially gelatinized polysaccharide in said suspension with a functionalizing agent under alkaline conditions, to obtain said functionalized polysaccharide, wherein said functionalized polysaccharide has a degree of substitution of from about 0.1 to about 0.3,
wherein said polyol is ethylene glycol, propylene glycol, glycerol, sorbitol or combinations thereof.

2. The process of claim 1, wherein said polysaccharide is chosen from a starch, a cellulose, a chitosan, a guar gum, a gellan gum, a xanthan gum, an agar, an agarose, an arabic gum, a pullulan, a dextran, a dextrin, a maltodextrin, a cyclodextrin and/or chosen from modified polysaccharides selected from the group consisting of hydroxypropyl starch, hydroxypropyl cellulose, hydroxypropyl methyl starch, hydroxypropyl methyl cellulose, ethyl-cellulose, methylcellulose, succinyl starch, octenyl starch and combinations thereof.

3. The process of claim 1, wherein said an alkaline solvent mixture of water and alcohol is a binary solvent mixture of water and alcohol or ternary solvent mixture of water, alcohol and polyol.

4. The process of claim 3, wherein said binary solvent mixture of water and alcohol comprises water and at least one of ethanol, methanol, isopropanol, or combinations thereof, and said ternary solvent mixture of water and alcohol comprises water, ethanol or methanol and propylene glycol or glycerol or propanol or combination thereof.

5. The process of claim 3, wherein said water or said alcohol is from about 5% to about 50% v/v of said binary or ternary solvent mixture.

6. The process of claim 3, wherein said polyol is from about 50% to about 95% v/v of said binary or ternary solvent mixture.

7. The process of claim 1, wherein said functionalizing agent is sodium chloroacetate, succinic anhydride, n-Octenyl succinic anhydride, acrylic acid, and combinations thereof.

8. The process of claim 1, further comprising step c') after step c):
    c') complexation of said functionalized polysaccharide with a divalent cation chosen from calcium, magnesium, zinc, aluminum, copper, or combinations thereof.

9. The process of claim 1, further comprising step d):
d) filtration of said functionalized polysaccharide and resuspension in alcohol, to obtain a resuspended functionalized polysaccharide.

10. The process of claim 9, further comprising step e):
e) neutralization of said resuspended functionalized polysaccharide, to obtain a neutralized functionalized polysaccharide.

11. The process of claim 10, further comprising step f):
f) washing of said neutralized functionalized polysaccharide, to obtain a precipitated functionalized polysaccharide.

12. The process of claim 11, further comprising step g):
g) drying of said precipitated functionalized polysaccharide, to obtain a dried functionalized polysaccharide.

13. The process of claim 1, wherein said functionalization is carboxymethylation.

* * * * *